(12) United States Patent
Hopkins et al.

(10) Patent No.: US 8,746,290 B2
(45) Date of Patent: Jun. 10, 2014

(54) SURGICAL CONSOLE

(75) Inventors: Mark A. Hopkins, Mission Viejo, CA (US); John C. Huculak, Mission Viejo, CA (US); Denis P. Turner, Vista, CA (US)

(73) Assignee: Novartis AG, Basel (CH)

( * ) Notice: Subject to any disclaimer, the term of this patent is extended or adjusted under 35 U.S.C. 154(b) by 1396 days.

(21) Appl. No.: 11/855,198

(22) Filed: Sep. 14, 2007

(65) Prior Publication Data

US 2008/0067902 A1 Mar. 20, 2008

Related U.S. Application Data

(60) Provisional application No. 60/845,387, filed on Sep. 18, 2006.

(51) Int. Cl.
*B05B 5/16* (2006.01)

(52) U.S. Cl.
USPC .................. 141/3; 141/4; 141/27; 604/24

(58) Field of Classification Search
USPC ......... 141/197, 21–27, 94, 95, 192, 198, 319, 141/329, 330; 604/23, 45, 24; 600/573; 128/204.22
See application file for complete search history.

(56) References Cited

U.S. PATENT DOCUMENTS

| 4,177,810 | A | | 12/1979 | Gourlandt |
| 4,262,686 | A | * | 4/1981 | Heim et al. ........................ 137/7 |
| 4,515,590 | A | | 5/1985 | Daniel |
| 5,019,037 | A | * | 5/1991 | Wang et al. ..................... 604/23 |
| 5,037,384 | A | | 8/1991 | Chang |
| 5,066,276 | A | * | 11/1991 | Wang ............................. 604/521 |
| 5,334,163 | A | | 8/1994 | Sinnett |
| 5,370,630 | A | | 12/1994 | Smidebush et al. |
| 5,806,513 | A | * | 9/1998 | Tham et al. ............. 128/204.22 |
| 6,073,759 | A | | 6/2000 | Lamborne et al. |
| 6,599,280 | B1 | * | 7/2003 | Pynson et al. ................ 604/403 |
| 6,997,904 | B2 | | 2/2006 | Sculati |
| 7,703,483 | B2 | * | 4/2010 | Hartman et al. ................ 141/27 |
| 2003/0209455 | A1 | | 11/2003 | Pynson et al. |
| 2006/0068031 | A1 | | 3/2006 | Miller et al. |

FOREIGN PATENT DOCUMENTS

| EP | 0960629 | * | 1/1999 | ............ A61M 16/12 |
| EP | 0960629 | A | 12/1999 | |
| EP | 1449559 | A | 8/2004 | |
| WO | 2004/058112 | A2 | 7/2004 | |
| WO | 2004071268 | A | 8/2004 | |
| WO | WO2004108533 | * | 12/2004 | ................ B65B 3/00 |

* cited by examiner

*Primary Examiner* — Jason Boeckmann
*Assistant Examiner* — Joel Zhou
(74) *Attorney, Agent, or Firm* — W. David Lee

(57) ABSTRACT

A surgical console having bottles containing retinal tamponading gases and an automatic gas filling module disposed therein for filling an automatic gas filling consumable is disclosed. The automatic gas filling module includes a pair of gas shutoff valves and a regulator connected in series with a port for connection to the automatic gas filling consumable.

2 Claims, 1 Drawing Sheet

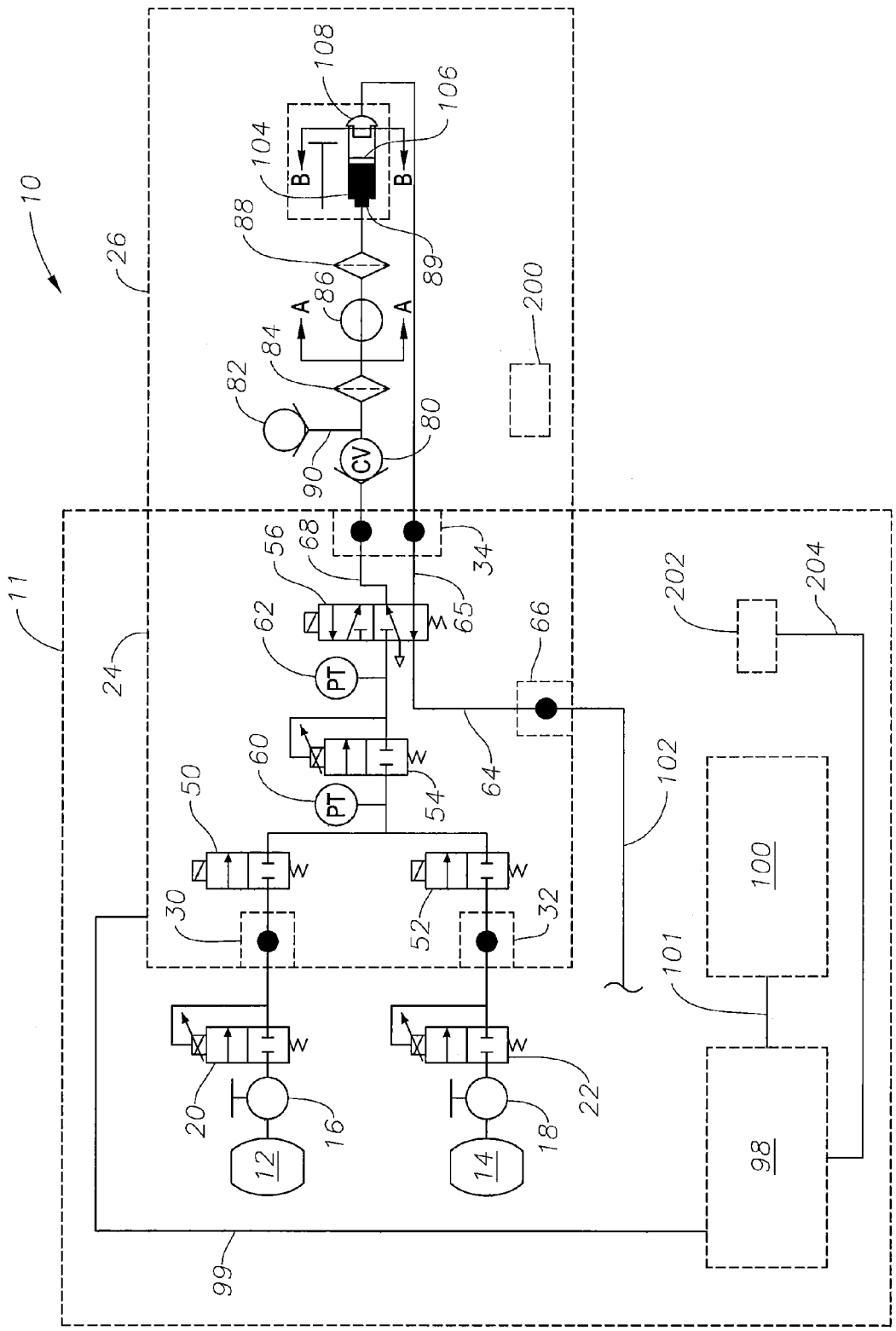

SURGICAL CONSOLE

This application claims the priority of U.S. Provisional Application Ser. No. 60/845,387 filed on Sep. 18, 2006.

FIELD OF THE INVENTION

The present invention generally pertains to vitreoretinal surgery and more particularly to improved systems for helping to perform fluid exchanges typically used in such surgeries.

DESCRIPTION OF THE RELATED ART

In a healthy human eye, the retina is physically attached to the choroid in a generally circumferential manner behind the pars plana. The vitreous humor, a transparent jelly-like material that fills the posterior segment of the eye, helps to cause the remainder of the retina to lie against, but not physically attach, to the choroid.

Sometimes a portion of the retina becomes detached from the choroid. Other times a portion of the retina may tear, allowing vitreous humor, and sometimes aqueous humor, to flow between the retina and the choroid, creating a build up of subretinal fluid. Both of these conditions result in a loss of vision.

To surgically repair these conditions, a surgeon typically inserts a vitrectomy probe into the posterior segment of the eye via a scleratomy, an incision through the sclera at the pars plana. The surgeon typically also inserts a fiber optic light source and an infusion cannula into the eye via similar incisions, and may sometimes substitute an aspiration probe for the vitrectomy probe. While viewing the posterior segment under a microscope and with the aid of the fiber optic light source, the surgeon cuts and aspirates away vitreous using the vitrectomy probe to gain access to the retinal detachment or tear. The surgeon may also use the vitrectomy probe, scissors, a pick, and/or forceps to remove any membrane that has contributed to the retinal detachment or tear. During this portion of the surgery, a saline solution is typically infused into the eye via the infusion cannula to maintain the appropriate intraocular pressure.

Next, the surgeon must manipulate the detached or torn portion of the retina to flatten against the choroid in the proper location. A soft tip cannula, forceps, or pick is typically utilized for such manipulation. Many surgeons also inject perfluorocarbon liquid as a retinal tamponading fluid into the posterior segment of the eye while aspirating the saline solution in the posterior segment to help cause the detached or torn portion of the retina to flatten against the choroid in the proper location. This procedure is typically referred to as a "fluid/perfluorocarbon" exchange. Other surgeons inject air as a retinal tamponading fluid into the posterior segment of the eye while aspirating the saline solution. This procedure is typically referred to as a "fluid/air" exchange. Finally, other surgeons inject a mixture of air and a gas such as $SF_6$, $C_3F_8$, or $C_2F_6$ as a retinal tamponading fluid into the posterior segment of the eye while aspirating the saline solution. This procedure is typically referred to as a "fluid/gas" exchange. As used herein, a "fluid" may include any liquid or gas that is suitable for use in the eye, including, but not limited to, saline solution with or without additives, silicone oil, a perfluorocarbon liquid, air, or a perfluorocarbon gas. The fluid exchange process is most typically performed by using a syringe filled with gas.

The process of filling the syringe with gas is currently time consuming. The process of filling the syringe with gas is a two person activity, requiring one person to be sterile, and one person not to be sterile. Often times, the coordination of activity between the two individuals results in the loss of gas and a waste of time, and, possibly, the violation of the sterile field.

As a result, a need still exists in vitreoretinal surgery for an improved system for helping to fill syringes with gas to be used in a fluid/gas exchange. The system should allow a scrub nurse to fill the gas syringe single handed, allow the nurse to maintain the integrity of the sterile field, eliminate the waste of expensive gas, provide early warning when gas bottles are depleted, and eliminate time lost as a result of mistakes.

SUMMARY OF THE INVENTION

The present invention comprises a method of filling a syringe with a retinal tamponading gas. An automatic gas filling consumable containing a syringe is fluidly coupled to a port of an ophthalmic surgical console. A user interface of the console is used to select a particular retinal tamponading gas. The syringe is filled with the retinal tamponading gas from the console. After filling, the syringe is removed from the automatic gas filling consumable for subsequent use by a surgeon.

BRIEF DESCRIPTION OF THE DRAWINGS

For a more complete understanding of the present invention, and for further objects and advantages thereof, reference is made to the following description taken in conjunction with the accompanying drawing in which FIG. 1 is a schematic view of a surgical system including an automatic gas filling module and an automatic gas filling consumable.

DETAILED DESCRIPTION OF THE PREFERRED EMBODIMENTS

The preferred embodiments of the present invention and their advantages are best understood by referring to FIG. 1 of the drawings. Surgical system 10 generally includes a surgical console 11 and an automatic gas filling consumable 26. Surgical system 10 is preferably an ophthalmic surgical system.

Surgical console 11 preferably includes a pressurized gas bottle 12 having an integral valve 16 and regulator 20, a pressurized gas bottle 14 having an integral valve 18 and regulator 22, an automatic gas filling module 24 having an automatic gas filling port 34, a microprocessor 98 electrically coupled to automatic gas filling module 24 via an interface 99, a graphical user interface 100 electrically coupled to microprocessor 98 via interface 101, and a pressurized air line 102 capable of providing pressurized air in a proportional manner. Pressurized gas bottle 12 preferably holds a first retinal tamponading gas such as, by way of example, $C_3F_8$. Pressurized gas bottle 14 preferably holds a second retinal tamponading gas such as, by way of example, $SF_6$. Gas bottles 12 and 14, valves 16 and 18, and regulators 20 and 22 are fluidly coupled with automatic gas filling module 24 via connection points 30 and 32. Likewise, automatic gas filling module 24 is fluidly coupled with automatic gas filling consumable 26 via automatic gas filling port 34.

Automatic gas filling module 24 preferably includes shut-off valves 50 and 52, each of which is fluidly coupled with a regulator 54. Regulator 54 is fluidly coupled to timing valve 56. A pair of pressure transducers 60 and 62 are positioned on either side of regulator 54 to monitor gas pressure and flow. Alternatively, pressure transducer 60 may be positioned between regulator 54 and transducer 62. Pressurized air line 102 is fluidly coupled to automatic gas filling module 24 via connection point 66, and is also fluidly coupled with timing valve 56 via a gas line 64. A gas line 68 fluidly couples timing valve 56 and automatic gas filling port 34. A gas line 65 fluidly couples gas line 64 and automatic gas filling port 34 via timing valve 56. Alternatively, timing valve 56 may be eliminated, and a shutoff valve (not shown) may be included on pressurized air line 102 instead.

Automatic gas filling consumable 26 preferably includes a check valve 80 fluidly coupled to automatic gas filling port 34 via gas line 68. A relief valve 82 is fluidly coupled with gas line 68 via a gas line 90. Gas line 68 also fluidly couples filter 84, stop cock 86, filter 88, and a distal end 89 of a syringe 104. Pressurized air line 102 is fluidly coupled to an end cap 108 of syringe 104 via gas lines 64 and 65.

Gas bottles 12 and 14 are installed in console 11 with valves 16 and 18 open, and with regulators 20 and 22 pre-set. During operation, a scrub nurse will insert a sterile automatic gas filling consumable 26 into automatic gas filling port 34 on automatic gas filling module 24. Preferably, an RFID tag 200 on consumable 26 will be read by an RFID receiver 202 within surgical console 11. RFID receiver 202 is electrically coupled to microprocessor 98 via an interface 204. Surgical console 11 will thus detect that consumable 26 is an automatic gas filling consumable, and will populate the graphical user interface 100 appropriately. Alternatively, population of graphical user interface 100 may be performed manually in the event that RFID is not available.

Using graphical user interface 100, the scrub nurse will then select the retinal tamponading gas to be used and initiate the automatic gas filling process. At this point, depending on the retinal tamponading gas selected, microprocessor 98 opens one of gas shutoff valves 50 or 52. Regulator 54 will regulate the gas to a preset pressure that will flow to timing valve 56. Pressure transducers 60 and 62 will be monitored to verify that sufficient gas pressure and flow are available (i.e. that the readings in pressure transducers 60 and/or 62 are at or near the set point of regulator 54). In the event that sufficient gas pressure and flow are not available, microprocessor 98 will signal the scrub nurse via graphical user interface 100 that the active gas bottle 12 or 14 needs to be replaced.

Next, timing valve 56 will be energized, and retinal tamponading gas will flow through automatic gas filling port 34 into automatic gas filling consumable 26, and into distal end 89 of syringe 104. Gas pressure will overcome the friction of a stopper 106 within syringe 104, and stopper 106 will travel toward end cap 108, filling syringe 104 with retinal tamponading gas. Pressurized air within pressurized air line 102 will be vented to atmosphere during this process.

Timing valve 56 will then be closed and pressurized air from pressurized air line 102 will be supplied to end cap 108 of syringe 104, overcoming the friction of stopper 106 and allowing retinal tamponading gas to flow through syringe 104, filter 88, stop cock 86, and filter 84. Relief valve 82 is overcome so that retinal tamponading gas is vented to atmosphere. Microprocessor 98 repeats this cycle of introducing gas to syringe 104, and purging gas from syringe 104, a sufficient number of times until the concentration of retinal tamponading gas within syringe 104 is at or near 100%. In the embodiment where timing valve 56 is not utilized, microprocessor 98 controls the opening, closing, and cycling of (a) either shutoff valve 50 or 52 and (b) the shutoff valve on pressurized air line 102 in a manner similar to that described above.

The scrub nurse will then remove end cap 108 from syringe 104 and will install a plunger (not shown) into syringe 104. The scrub nurse then closes stop cock 86 and disconnects consumable 26 from surgical console 11 at section A. Gas filled syringe 104 is then presented to the surgeon for final mixing and administration. The portion of automatic gas filling consumable 26 that remains on console 11 will be removed and discarded when the case is complete.

From the above, it may be appreciated that the present invention provides improved apparatus and methods for helping to fill a syringe with gas and helping to perform fluid/gas exchanges in vitreoretinal surgery. The system allows a scrub nurse to fill a gas syringe single handed, allows the nurse to maintain the integrity of the sterile field, eliminates the waste of expensive gas, provides an early warning when gas bottles are near depleted, and saves time lost due to mistakes.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A method of filling an automatic gas filling consumable with a retinal tamponading gas, comprising the steps of:
   providing an ophthalmic surgical system comprising an ophthalmic surgical console and said automatic gas filling consumable, said surgical console comprising a first pressurized gas bottle containing a first retinal tamponading gas, a second pressurized gas bottle containing a second retinal tamponading gas, an automatic gas filling port, a graphical user interface, a pressurized air line, and a computer all disposed within said surgical console, and said automatic gas filling consumable comprising a syringe having an end cap;
   fluidly coupling said automatic gas filling consumable to said automatic gas filling port of said surgical console;
   using said graphical user interface to select between said first retinal tamponading gas and said second retinal tamponading gas stored in said surgical console;
   in response to said selection, using said computer to fill said syringe with said selected one of said first and second retinal tamponading gases from said surgical console;
   using said computer to purge said selected one of said first and second retinal tamponading gases and air disposed within said syringe to atmosphere using said pressurized air line fluidly coupled to said end cap;
   removing said syringe from said automatic gas filling consumable; and
   removing a remainder of said automatic gas filling consumable from said surgical console.

2. The method of claim 1 further comprising the step of:
   repeating said step of using said computer to fill and said step of using said computer to purge until said syringe contains substantially only said selected one of said first and second retinal tamponading gases and none of said air.

* * * * *